United States Patent
Naumann et al.

(10) Patent No.: US 6,814,761 B1
(45) Date of Patent: Nov. 9, 2004

(54) DIRECT HAIR COLORANTS

(75) Inventors: Frank Naumann, Duesseldorf (DE); David Rose, Hilden (DE); Bernd Meinigke, Leverkusen (DE); Horst Hoeffkes, Duesseldorf (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 279 days.

(21) Appl. No.: 10/088,062

(22) PCT Filed: Sep. 8, 2000

(86) PCT No.: PCT/EP00/08774

§ 371 (c)(1),
(2), (4) Date: Aug. 15, 2002

(87) PCT Pub. No.: WO01/21144

PCT Pub. Date: Mar. 29, 2001

(30) Foreign Application Priority Data

Sep. 17, 1999 (DE) .......................................... 199 44 528

(51) Int. Cl.⁷ .................................................. A61K 7/13
(52) U.S. Cl. ...................... 8/405; 8/408; 8/414; 8/415; 564/431; 424/70.6
(58) Field of Search ........................... 8/405, 408, 414, 8/415; 564/431; 424/70.6

(56) References Cited

U.S. PATENT DOCUMENTS

| | | | |
|---|---|---|---|
| 3,632,582 A | 1/1972 | Bil ........................... | 260/247.5 |
| 3,944,612 A | 3/1976 | Bil ............................. | 260/573 |
| 4,865,774 A | 9/1989 | Fabry et al. ................. | 252/554 |
| 4,931,066 A | 6/1990 | Grollier et al. ............... | 8/410 |
| 4,931,218 A | 6/1990 | Schenker et al. ........... | 252/551 |
| 5,294,726 A | 3/1994 | Behler et al. ................. | 554/98 |
| 5,414,128 A | 5/1995 | Steckelberg et al. ......... | 564/406 |
| 5,534,267 A | 7/1996 | Neunhoeffer et al. ....... | 424/701 |
| 6,099,592 A | 8/2000 | Vidal et al. ................... | 8/409 |
| 6,114,532 A | 9/2000 | Ries et al. ................... | 546/162 |

FOREIGN PATENT DOCUMENTS

| | | |
|---|---|---|
| DE | 37 23 354 | 1/1989 |
| DE | 37 25 030 | 2/1989 |
| DE | 39 26 344 | 2/1991 |
| DE | 35 28 882 | 4/1996 |
| DE | 198 04 085 | 8/1999 |
| EP | 0 740 931 | 11/1996 |
| GB | 1 206 491 | 9/1970 |
| GB | 1 349 118 | 3/1974 |
| WO | WO 94/08970 | 4/1994 |

OTHER PUBLICATIONS

The Science of Hair Care, Chapter 7, pp. 235–261, published in vol. 7 of Dermatology, Marcel Dekker Inc. NY/Basle (1986).

The Science of Hair Care, Chapter 8, pp. 263–286, published in vol. 7 of Dermatology, Marcel Dekker Inc. NY/Basle (1986).

EU Inventory of Cosmetic Ingredients, Colipa, Mar. 1996 on diskette.

*Primary Examiner*—Samuel Barts
(74) *Attorney, Agent, or Firm*—Stephen D. Harper; Gregory M. Hill

(57) ABSTRACT

The present invention provides a coloring or tinting composition containing one or more certain 2-nitro-p-phenylene diamine derivatives as substantive dyes. The 2-nitro-p-phenylene diamine derivatives 1-(N-cycloheptylamino)-2-nitro-4-aminobenzene and 1-(N-cyclooctylamino)-2-nitro-4-aminobenzene are preferred.

21 Claims, No Drawings

DIRECT HAIR COLORANTS

CROSS REFERENCE TO RELATED APPLICATIONS

This application is a national stage application under 35 U.S.C. § 371 of international application PCT/EP00/08774 filed on Sep. 8, 2000, the international application not being published in English. This application also claims priority under 35 U.S.C. §119 to DE 199 44 528.1 filed on Sep. 17, 1999.

BACKGROUND OF THE INVENTION

This invention relates to new substantive dyes, to preparations for coloring and tinting keratin fibers, more especially human hair, containing these dyes and to the use of these preparations.

Preparations for tinting and coloring hair are an important type of cosmetic product. They may be used to give the natural color of the hair a light or relatively dark shade, to obtain a totally different hair color or to cover unwanted color tones, for example gray tones, according to the wishes of the particular user. Conventional hair colorants are formulated either on the basis of oxidation dyes or on the basis of substantive dyes according to the required color or the permanence thereof. In many cases, combinations of oxidation dyes and substantive dyes are also used to obtain special shades.

Good dyes are distinguished by high coloring strength. They are also required to show high fastness to perspiration, washing and light. In addition, they are expected to be toxicologically and dermatologically safe. It is also of advantage if the substances are highly soluble in various basic formulations.

Colorants based on oxidation dyes lead to bright and permanent color tones. However, they do involve the use of powerful oxidizing agents such as, for example, hydrogen peroxide solutions. This can damage the hair to be colored. Such damage then has to be repaired with suitable hair-care products. In addition, contact of the skin with these colorants can produce unwanted reactions in very sensitive people.

Colorants based on substantive dyes do not require oxidizing agents and can be better formulated at pH values around the neutral point. However, a major disadvantage of colorants based on substantive dyes is the poor fastness to washing of the colored hair. Consequently, the ability of the dye molecules to attach themselves to the hair and the luster of the colored hair are not entirely satisfactory in many cases.

To develop fashionable colors, red color tones have to be obtained. This is frequently achieved by the use of 2-nitro-p-phenylenediamine derivatives. However, these derivatives are often inadequately soluble or dispersible in water. If the dye cannot be solubilized in the coloring medium, uneven colors are the result. There is also a high risk of only weak colors being obtained.

To improve level dyeing and to broaden the range of shades, substantive dyes are also commonly used in oxidation hair colors. Unfortunately, the substantive dyes normally used show poor stability to reducing and oxidizing agents.

Accordingly, there is still a demand for substantive dyes which do not have any of the disadvantages mentioned above.

It has now surprisingly been found that certain 2-nitro-p-phenylenediamine derivatives satisfy the requirements substantive dyes are expected to meet to a high degree.

SUMMARY OF THE INVENTION

In a first embodiment, therefore, the present invention relates to preparations for coloring keratin fibers, more particularly human hair, which contain at least one 2-nitro-p-phenylenediamine derivative corresponding to formula (I):

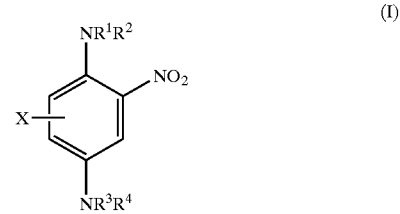

in which $R^1$ to $R^4$ independently of one another represent hydrogen, a $C_{1-4}$ hydroxyalkyl group or a saturated, mono- or polyunsaturated $C_{7-8}$ ring which may optionally be substituted by a $C_{1-4}$ alkyl group, a halogen atom, a hydroxy group or an amino group and X is hydrogen or a halogen atom, with the proviso that at least one of the substituents $R^1$ to $R^4$ is a $C_{7-8}$ ring, in a carrier suitable for coloring.

DETAILED DESCRIPTION OF THE INVENTION

Example of the $C_{1-4}$ alkyl groups mentioned as substituents in the compounds according to the invention are the methyl, ethyl, propyl, isopropyl and butyl groups. Ethyl and methyl are preferred alkyl groups. A methyl group is particularly preferred. Preferred examples of a $C_{1-4}$ hydroxyalkyl group can be a hydroxymethyl, 2-hydroxyethyl, 3-hydroxy-propyl or 4-hydroxybutyl group. A 2-hydroxyethyl group is particularly preferred. According to the invention, examples of a halogen atom are an F, Cl or Br atom, a Cl atom being particularly preferred. Preferred ring systems are the cycloheptyl ring, the cyclooctyl ring and methyl-, hydroxy- or amino-substituted derivatives thereof. The unsubstituted cycloheptyl ring and the unsubstituted cyclooctyl ring are particularly preferred.

Compounds of formula (I) in which the substituents $R^2$ to $R^4$ are hydrogen are particularly preferred. However, compounds of formula (I) where $R^1$ and $R^3$ each represent a ring substituent and compounds where one of the substituents $R^1$ or $R^3$ is a ring system and the other is a 2-hydroxyethyl group are also preferred.

Compounds of formula (I) with a chlorine substituent (X) in position 3, 5 or 6 are also preferred.

Compounds of formula (I) where X is a hydrogen atom are particularly preferred.

Most particularly preferred compound of formula (I) are 1-(N-cycloheptylamino)-2-nitro-4-aminobenzene and 1-(N-cyclooctylamino)-2-nitro-4-aminobenzene.

In a first preferred embodiment, the preparations according to the invention are preparations intended to produce only temporary coloring of the fibers. Corresponding preparations are commonly known as tinting preparations. This embodiment also encompasses, for example, hair treatment preparations with which the hair is intended to be not only temporarily colored, but also given a certain style. Corresponding preparations are known as tinting lotions.

Since the preparations in question are normally formulated without the assistance of oxidizing components, especially hydrogen peroxide, the preparations according to the invention in this embodiment may be free from oxidation dye precursors.

Although the compounds corresponding to formula (I) may also be used as sole dye component, the preparations according to this embodiment preferably still contain at least one other dye of the substantive type.

Substantive dyes are normally nitrophenylenediamines, nitro-aminophenols, azo dyes, anthraquinones or indophenols. Preferred substantive dyes are the compounds known under the International names or trade names of HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17 and also 1,4-bis-(β-hydroxyethyl)-amino-2-nitrobenzene, 4-amino-2-nitrodiphenylamine-2'-carboxylic acid, 6-nitro-1,2,3,4-tetrahydro-quinoxaline, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene. The preparations according to the invention in this embodiment preferably contain the substantive dyes in a quantity of 0.01 to 20% by weight, based on the colorant as a whole.

The preparations according to the invention may also contain naturally occurring dyes such as, for example, henna red, henna neutral, henna black, camomile blossom, sandalwood, black tea, black alder bark, sage, logwood, madder root, catechu, sedre and alkanet.

Other dye components present in the colorants according to the invention include indoles and indolines and physiologically compatible salts thereof. Preferred examples are 5,6-dihydroxyindole, N-methyl-5,6-dihydroxyindole, N-ethyl-5,6-dihydroxyindole, N-propyl-5,6-dihydroxyindole, N-buyl-5,6-dihydroxyindole, 5,6-dihydroxyindole-2-carboxylic acid, 6-hydroxyindole, 6-aminoindole and 4-aminoindole. Other preferred examples are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 6-hydroxy-indoline, 6-aminoindoline and 4-aminoindoline.

In a second preferred embodiment, the claimed preparations are hair colorants for the permanent coloring of hair. These compositions contain at least one oxidation dye precursor of the primary intermediate type. These generally colorless compounds react with one another under the effect of oxidizing agents or atmospheric oxygen, optionally with the aid of special enzymes or metal ions as catalysts, to form the required dyes. However, in order in particular to form natural hair colors, combinations of several primary intermediates are generally used. In addition, so-called secondary intermediates are generally additionally used. Secondary intermediates react with the primary intermediates under the effect of oxidizing agents which leads to new colors or to a shading of the color. According to the invention, both a single secondary intermediate and several secondary intermediates may be used in combination with one or more primary intermediates.

According to the invention, preferred primary intermediates are p-phenylenediamine, p-toluylenediamine, p-aminophenol, o-aminophenol, 1-(2'-hydroxyethyl)-2,5-diaminobenzene, N,N-bis-(2-hydroxyethyl)-p-phenylenediamine, 2-(2,5-diaminophenoxy)-ethanol, 1-phenyl-3-carboxyamido-4-amino-5-pyrazolone, 4-amino-3-methylphenol, 2,4,5,6-tetraaminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2-hydroxymethylamino-4-aminophenol, bis-(4-aminophenyl)-amine, 4-amino-3-fluorophenol, 2-aminomethyl-4-aminophenol, 2-hydroxymethyl-4-aminophenol, 4-amino-2-((diethylamino)-methyl)-phenol, bis-(2-hydroxy-5-aminophenyl)-methane, 1,4-bis-(4-aminophenyl)-diazacycloheptane, 1,3-bis-(N-(2-hydroxyethyl)-N-(4-aminophenylamino))-2-propanol, 4-amino-2-(2-hydroxyethoxy)-phenol, 1,10-bis-(2,5-diamino-phenyl)-1,4,7,10-tetraoxadecane and 4,5-diaminopyrazole derivatives according to EP 0 740 931 or WO 94/08970 such as, for example, 4,5-diamino-1-(2'-hydroxyethyl)-pyrazole.

According to the invention, particularly preferred primary intermediates are p-phenylenediamine, p-toluylenediamine, p-aminophenol, 1-(2'-hydroxyethyl)-2,5-diaminobenzene, N,N-bis-(2-hydroxyethyl)-p-phenylenediamine, 4-amino-3-methylphenol, 4-amino-2-((diethylamino)-methyl)-phenol, 2-aminomethyl-4-aminophenol, 2,4,5,6-tetraaminopyrimidine, 2-hydroxy-4,5,6-triaminopyrimidine, 4-hydroxy-2,5,6-triaminopyrimidine and 4,5-diamino-1-(2'-hydroxyethyl)-pyrazole.

According to the invention preferred secondary intermediates are m-aminophenol and derivatives thereof such as, for example, 5-amino-2-methylphenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxy-ethyl)-amino-2-methylphenol, 3-(diethylamino)-phenol, N-cyclo-pentyl-3-aminophenol, 1,3-dihydroxy-5-(methylamino)-benzene, 3-(ethylamino)-4-methylphenol and 2,4-dichloro-3-aminophenol, o-aminophenol and derivatives thereof, m-diaminobenzene and derivatives thereof such as, for example, 2,4-diaminophenoxyethanol, 1,3-bis-(2,4-diaminophenoxy)-propane, 1-methoxy-2-amino-4-(2'-hydroxyethylamino)-benzene, 1,3-bis-(2,4-diaminophenyl)-propane, 2,6-bis-(2-hydroxyethylamino)-1-methyl-benzene and 1-amino-3-bis-(2'-hydroxyethyl)-aminobenzene, o-diaminobenzene and derivatives thereof such as, for example, 3,4-diaminobenzoic acid and 2,3-diamino-1-methylbenzene, di- and trihydroxybenzene derivatives such as, for example, resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene, pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diamino-pyridine, 2,3-diamino-6-methoxypyridine and 3,5-diamino-2,6-dimethoxypyridine, naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihdroxynaphthalene, 1,7-dihdroxynaphthalene, 1,8-dihdroxynaphthalene, 2,7-dihdroxynaphthalene and 2,3-dihdroxynaphthalene, morpholine derivatives such as, for example, 6-hydroxybenzomorpholine and 6-aminobenzomorpholine, quinoxaline derivatives such as, for example, 6-methyl-1,2,3,4-tetrahydroquinoxaline, pyrazole derivatives such as, for example, 1-phenyl-3-methylpyrazol-5-one, indole derivatives such as, for example, 4-hydroxyindole, 6-hydroxyindole and 7-hydroxyindole, methylenedioxybenzene derivatives such as, for example, 1-hydroxy-3,4-methylenedioxybenzene, 1-amino-3,4-methylenedioxy-benzene and 1-(2'-hydroxyethyl)-amino-3,4-methylenedioxy-benzene.

According to the invention, other preferred secondary intermediates are 3-dimethylaminophenol, 2,4-dihydroxyaniline, 8-amino-6-methoxy-quinoline, 2-amino-5-naphthol-1,7-disulfonic acid, 3,5-diaminobenzamide, 3-methylsulfonylamino-2-methylaniline, 5,6-dihydroxybenzimidazole, 2,2'-dihydroxybenzylamine, 3,5, 3',5'-tetraamino-2,2'-dimethoxydiphenyl, 3,5-diamino-p-chlorobenzotrifluoride, 4-methyl-3-aminophenol, 2,4-diamino-3-chlorophenol, 1-amino-3-di-(2-hydroxyethylamino)-4-ethoxybenzene, 2,4-dimethylresorcinol, bis-(2,4-diaminophenoxy)-methane, 2,6-bis-(hydroxy-ethyl)-pyridine, 4-hydroxy-3-methoxybenzylalcohol, 8-hydroxyquinoline, 4-hydroxy-3-methoxybenzylamine, 4-ethylresorcinol, 2-methylthio-5-aminophenol, 5-[(3-hydroxypropyl)amino]-2-methylphenol, 2,6-dimethoxy-3-aminophenol and 2,6-diamino-3-methylthiotoluene.

According to the invention, particularly preferred secondary intermediates are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methyl resorcinol, 5-methyl resorcinol, 2,5-dimethyl resorcinol and 2,6-dihydroxy-3,4-dimethylpyridine.

According to the invention, it may be preferable to use primary and secondary intermediates which do not require any oxidizing agents other than air to form the colors.

Besides the compounds corresponding to formula (I), the primary intermediate and optionally secondary intermediates, the preparations according to the invention of this embodiment may if desired contain other substantive dyes for shading purposes. Reference is made at this juncture to the above list.

The hair colorants according to the invention contain both the primary intermediates and the secondary intermediates in a quantity of preferably 0.005 to 20% by weight, based on the colorant without the oxidizing agent preparation. The primary and secondary intermediates are generally used in a substantially equimolar ratio to one another. Although it has proved to be of advantage to use the primary and secondary intermediates in an equimolar ratio, there is no disadvantage in using a certain excess of individual oxidation dye precursors so that primary and secondary intermediates may be present in a molar ratio of 1:0.5 to 1:2.

The oxidation dye precursors or the substantive dyes do not have to be single compounds. On the contrary, other components may be present in small quantities in the hair colorants according to the invention due to the processes used to produce the individual dyes providing these other components do not adversely affect the coloring result or have to be ruled out for other reasons, for example toxicological reasons.

So far as the dyes suitable for use in the hair colorants and tinting preparations according to the invention are concerned, reference is also expressly made to the work by Ch. Zviak, The Science of Hair Care, Chapter 7 (pages 248–250; substantive dyes) and Chapter 8, pages 264–267; oxidation dye precursors), published as Volume 7 of the Series "Dermatology" (Ed.: Ch. Culnan and H. Maibach), Marcel Dekker Inc., New York/Basle, 1986, and to the "Europäische Inventar der Kosmetik-Rohstoffe" published by the Europäische Gemeinschaft and available in disk form from the Bundesverband Deutscher Industrie- und Handelsunternehmen für Arzneimittel, Reformwaren und Körperpflegemittel d.V., Mannheim.

In a preferred embodiment, the preparations according to the invention also contain anionic, nonionic or—more particularly—cationic polymers, especially if they are also intended to have conditioning or setting properties.

Cationic polymers suitable as conditioning agents contain cationic groups within the polymer chain. These groups may be part of the polymer chain although they may also be positioned in side chains attached to a main chain by intermediate links. Typical cationic groups contain quaternary nitrogen or phosphorus atoms. Groups containing quaternary nitrogen atoms are preferred. The quaternary nitrogen atoms may carry four different substituents or partly identical substituents and may be part of a ring system. Preferred cationic groups are ammonium and imidazolinium groups.

The following are examples of such polymers:

Quaternized cellulose derivatives commercially available under the names of Celquat® and Polymer JR®. The compounds Celquat® H 100, Celquat L 200 and Polymer JR®400 are preferred quaternized cellulose derivatives.

Copolymers of vinyl pyrrolidone with quaternized derivatives of dialkylaminoacrylate and methacrylate, such as vinyl pyrrolidone/dimethylaminomethacrylate copolymers quaternized, for example, with diethyl sulfate and the copolymer of vinyl pyrrolidone and methacrylamidopropyl trimethyl ammonium chloride. Compounds such as these are commercially available under the names of Gafquat®734, Gafquat®755 and Gafquat® HS100.

Copolymers of vinyl pyrrolidone with vinyl imidazolium methochloride which are commercially available under the name of Luviquat®.

Polymeric dimethyl diallyl ammonium salts and copolymers thereof with acrylic acid and with esters and amides of acrylic acid and methacrylic acid. The products commercially available under the names of Merquat®100 (poly(dimethyl diallyl ammonium chloride)), Merquat®550 (dimethyl diallyl ammonium chloride/acrylamide copolymer) and Merquat® 280 (dimethyl diallyl ammonium chloride/acrylic acid copolymer) are examples of such cationic polymers.

Quaternized guar derivatives commercially available under the names of Cosmedia Guar® and Jaguar®. Preferred guar derivatives are, for example, Cosmedia Guar® C-261 and Jaguar® C 13-S.

Cationically derivatized silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as amodimethicone), SM-2059 (manufacturer: General Electric), SLM-55067 (manufacturer: Wacker) and Abil® Quat 3270 and 3272 (manufacturer: Th. Goldschmidt; diquaternary polydimethyl siloxanes, Quaternium-80).

Chitosan and derivatives thereof.

Quaternized polyvinyl alcohol.

The polymers with quaternary nitrogen atoms in the main polymer chain known by the names of Polyquaternium 2, Polyquaternium 17, Polyquaternium 8 and Polyquaternium 27.

Cationic polymers from the first four groups mentioned are particularly preferred, Polyquaternium 2, Polyquaternium 10 and Polyquaternium 22 being most particularly preferred.

The cationic polymers are preferably present in the preparations according to the invention in quantities of 0.1 to 5% by weight, based on the preparation as a whole.

The following are examples of suitable nonionic polymers:

Vinyl pyrrolidone/vinyl ester copolymers of the type marketed for example under the trade mark Luviskol® (BASF). Luviskol® VA 64 and Luviskol® VA, both vinyl pyrrolidone/vinyl acetate copolymers, are preferred nonionic polymers.

Cellulose ethers, such as the hydroxypropyl cellulose, hydroxyethyl cellulose and methyl hydroxypropyl cellulose marketed under the trade marks Culminal® and Benecel® (AQUALON).

Shellac.

Polyvinyl pyrrolidones of the type marketed under the name Luviskol® (BASF).

The following are examples of suitable anionic polymers:

Copolymers of acrylic acid and/or methacrylic acid or esters thereof with $C_{10-30}$ alkyl acrylates of the type marketed, for example, under the name Pemulen®.

Polymers and copolymers of crotonic acid with esters and amides of acrylic and methacrylic acid, such as vinyl acetate/crotonic acid and vinyl acetate/vinyl propionate/crotonic acid copolymers. Compounds of this type are marketed under the names Resyn® (NATONAL STARCH), Luviset® (BASF) and Gafset® (GAF). The products Luviset® CA-66 and Luviset® CAP may be preferable.

Vinyl pyrrolidone/vinyl acrylate copolymers obtainable, for example, under the trade mark Luviflex® (BASF). A preferred polymer is the vinyl pyrrolidone/acrylate terpolymer obtainable under the name Luviflex® VBM-35 (BASF).

Acrylic acid/ethyl acrylate/N-tert.butyl acrylamide terpolymers marketed, for example, under the name Ultrahold® strong (BASF) and methacrylic acid/ethyl acrylate/t-butyl acrylate terpolymers marketed under the name Luvimer® 100P (BASF).

It may be of preferred to use anionic, nonionic or cationic polymers in hair colorants that are free from oxidation dye precursors.

To produce the colorants according to the invention, the substantive dyes and the oxidation dye precursors, if any, are incorporated in a suitable water-containing carrier. For coloring hair, such carriers are, for example, creams, emulsions, gels or even surfactant-containing foaming solutions, for example shampoos, foam aerosols or other formulations suitable for application to the hair.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the preparations according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide and hydroxyl groups may also be present in the molecule. The following are examples of suitable anionic surfactants—in the form of the sodium, potassium and ammonium salts and the mono-, di- and trialkanol-ammonium salts containing 2 or 3 carbon atoms in the alkanol group:

linear fatty acids containing 10 to 22 carbon atoms (soaps), ether carboxylic acids corresponding to the formula R—O—$(CH_2$—$CH_2O)_x$—$CH_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 1.8 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O$(CH_2$—$CH_2O)_x$—$SO_3H$, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —$COO^{(-)}$ or —$SO_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one —COOH or —$SO_3H$ group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl amino-propionate, cocoacyl aminoethyl aminopropionate and $C_{12-18}$ acyl sarcosine.

Nonionic surfactants contain, for example, a polyol group, a poly-alkylene glycol ether group or a combination of polyol and polyglycol ether groups as the hydrophilic group. Examples of such compounds are
- products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group,
- $C_{12-22}$ fatty acid monoesters and diesters of products of the addition of 1 to 30 moles of ethylene oxide onto glycerol,
- $C_{8-22}$ alkyl mono- and oligoglycosides and ethoxylated analogs thereof,
- products of the addition of 5 to 60 moles of ethylene oxide onto castor oil and hydrogenated castor oil,
- products of the addition of ethylene oxide onto sorbitan fatty acid esters and
- products of the addition of ethylene oxide onto fatty acid alkanolamides.

Examples of cationic surfactants suitable for use in the hair treatment preparations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex® and the products marketed under the trade name of Dehyquart®, such as Dehyquart® AU-46, are also readily biodegradable.

One example of a quaternary sugar derivative suitable for use as a cationic surfactant is the commercially available product Glucquat®100 (INCI name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

The hair treatment preparations according to the invention preferably may also contain a conditioning agent selected from the group consisting of cationic surfactants, cationic polymers, alkyl amidoamines, paraffin oils and synthetic oils.

Cationic polymers can be preferred conditioning agents. Reference is made in this connection to the polymers mentioned in the foregoing.

Other suitable conditioning agents are silicone oils, more particularly dialkyl and alkylaryl siloxanes such as, for example, dimethyl polysiloxane and methylphenyl polysiloxane and alkoxylated and quaternized analogs thereof. Examples of such silicones are the products marketed by Dow Corning under the names of DC 190, DC 200, DC 344, DC 345 and DC 1401 and the commercial products Q2-7224 (manufacturer: Dow Corning; a stabilized trimethyl silyl amodimethicone), Dow Corning® 929 Emulsion (containing a hydroxylamino-modified silicone which is also known as amodimethicone), SM-2059 (manufacturer: General Electric), SLM-55067 (manufacturer: Wacker) and Abil® Quat 3270 and 3272 (manufacturer: Th. Goldschmidt; diquaternary polydimethyl siloxanes, quaternium-80).

Other suitable conditioning agents are paraffin oils, synthetically produced oligomeric alkenes and vegetable oils, such as jojoba oil, sunflower oil, orange oil, almond oil, wheatgerm oil and peach kernel oil.

Phospholipids, for example soya lecithin, egg lecithin and kephalins, are also suitable hair-conditioning compounds.

Other active substances, auxiliaries and additives are, for example,
- thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol,
- structurants, such as glucose and maleic acid,
- protein hydrolyzates, more particularly elastin, collagen, keratin, milk protein, soya protein and wheat protein hydrolyzates, condensation products thereof with fatty acids and quaternized protein hydrolyzates,
- perfume oils, dimethyl isosorbide and cyclodextrins, solubilizers, such as ethanol, isopropanol, ethylene glycol, propylene glycol, glycerol and diethylene glycol, antidandruff agents, such as Piroctone Olamine and Zinc Omadine, other substances for adjusting the pH value, active substances, such as panthenol, pantothenic acid, allantoin, pyrrolidone carboxylic acids and salts thereof, plant extracts and vitamins, cholesterol, sun protection factors, consistency factors, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, pearlizers, such as ethylene glycol mono- and distearate, propellents, such as propane/butane mixtures, $N_2O$, dimethyl ether, $CO_2$ and air, antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

In principle, the preparations according to the invention may be formulated in such a way that they may either remain on the hair or may be rinsed out.

In a preferred embodiment, the preparations according to the invention are formulated to remain on the hair. This is the case with so-called tinting preparations in particular, but also with preparations which are additionally intended to have a setting effect.

In a second embodiment, the present invention relates to the use of the preparations according to the invention for coloring and tinting keratin fibers, more particularly human hair.

In a third embodiment, the present invention relates to the compounds 1-(N-cycloheptylamino)-2-nitro-4-aminobenzene and 1-(N-cyclooctylamino)-2-nitro-4-aminobenzdene.

The following Examples are intended to illustrate the invention.

EXAMPLES

1. Preparation of 1-(N-cycloheptylamino)-2-nitro-4-aminobenzene

A mixture of 3.12 g (0.020 mol) of 4-fluoro-3-nitroaniline, 2.28 g (0.022 mol) of cycloheptylamine and 1.7 g (0.020 mol) of sodium hydrogen carbonate was refluxed for 3 hours in 5 ml of water and 5 ml of 2-propanol. After cooling to room temperature, the residues were filtered off and the filtrate was extracted with chloroform. The solvent was removed in vacuo and the residue was recrystallized from 20% hydrochloric acid. A green-brown solid melting at 153° C. was obtained.

2. Preparation of 1-(N-cyclooctylamino)-2-nitro-4-aminobenzene

A mixture of 3.12 g (0.020 mol) of 4-fluoro-3-nitroaniline, 2.57 g (0.022 mol) of cyclooctylamine and 1.7 g (0.020 mol) of sodium hydrogen carbonate was refluxed for 3 hours in 5 ml of water and 5 ml of 2-propanol. After cooling to room temperature, the residues were filtered off and the filtrate was extracted with chloroform. The solvent was removed in vacuo and the residue was recrystallized from 20% hydrochloric acid. A yellow-green solid melting at 161° C. was obtained.

3. Hair Coloring Creams Containing Substantive Dye

| Mixture A | |
|---|---|
| Cetearyl alcohol | 1.00 g |
| Fatty alcohol mixture based on coconut oil | 1.00 g |
| Akypo ® RLM 45 N[1] | 1.10 g |
| p-Hydroxybenzoic acid propyl ester | 0.05 g |
| p-Hydroxybenzoic acid methyl ester | 0.15 g |
| Water | 70.00 g |

[1]lauryl alcohol containing ca. 4.5 mol ethylene oxide/acetic acid sodium salt (ca. 82% active substance; INCI name: Sodium Laureth-6 Carboxylate) (KAO, Chem-Y)

The substances were melted at 80° C., mixed with water heated to 80° C. and emulsified with vigorous stirring. The emulsion was then cooled with vigorous stirring.

| Mixture B | |
|---|---|
| Ammonium sulfate | 1.00 g |
| Substantive dye corresponding to formula (I) | 1.00 g |
| Ammonia (25% solution) | to pH 9.0 |
| Water | 10.00 g |

The dyes were dissolved in water heated to 50° C. to which the ammonium sulfate and ammonia had been added.

The dye solution (mixture B) was added to the emulsion (mixture A), adjusted to pH 9 with ammonia and made up with water to 100 g. The whole was then stirred until room temperature was reached.

The coloring cream thus obtained was applied to 5 cm long tresses of standardized 80% gray, but not specially pretreated human hair and left thereon for 30 minutes at 32° C. The hair was then rinsed, washed with a typical hair shampoo and dried.

The results of the coloring tests are set out in Table I:

| Substantive dye | Shade of the colored hair |
|---|---|
| 1-(N-cycloheptylamino)-2-nitro-4-aminobenzene | Gray red |
| 1-(N-cyclooctylamino)-2-nitro-4-aminobenzene | Flat red |

What is claimed is:

1. A composition for coloring or tinting keratin fibers comprising at least one 2-nitro-p-phenylenediamine derivative corresponding to formula (I) as a substantive dye:

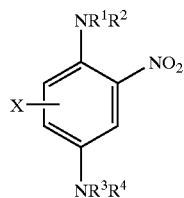

wherein R¹ to R⁴, independently of one another, represent hydrogen, a $C_{1-4}$ hydroxyalkyl group or a saturated, monounsaturated or polyunsaturated $C_{7-8}$ ring, wherein the $C_{7-8}$ ring may be optionally substituted by a $C_{1-4}$ alkyl group, a halogen atom, a hydroxy group or an amino group or combinations thereof, and wherein at least one of the substituents R¹ to R⁴ is the $C_{7-8}$ ring; and wherein X is hydrogen or a halogen atom.

2. The composition of claim 1 wherein R¹ is a cycloheptyl ring.

3. The composition of claim 1 wherein R¹ is a cyclooctyl ring.

4. The composition of claim 1 wherein X is hydrogen.

5. The composition of claim 1 wherein R² to R⁴ are hydrogen.

6. The composition of claim 5 wherein the compound corresponding to formula (I) comprises 1-(N-cycloheptylamino)-2-nitro-4-aminobenzene or 1-(N-cyclooctylamino)-2-nitro-4-aminobenzene, or combinations thereof.

7. The composition of claim 6 wherein the composition is free from oxidation dye precursors.

8. The composition of claim 1 wherein the compound corresponding to formula (I) comprises 1-(N-cycloheptylamino)-2-nitro-4-aminobenzene.

9. The composition of claim 1 wherein the compound corresponding to formula (I) comprises 1-(N-cyclooctylamino)-2-nitro-4-aminobenzene.

10. The composition of claim 1 wherein the composition is free from oxidation dye precursors.

11. The composition of claim 10 wherein the composition is formulated to remain on the hair.

12. The composition of claim 11 wherein the composition is a hair-setting preparation.

13. The composition of claim 1 further comprising at least one primary intermediate.

14. The composition of claim 13 wherein the primary intermediate comprises p-phenylenediamine, p-toluylenediamine, p-aminophenol, 1-(2'-hydroxyethyl)-2, 5-diaminobenzene, N,N-bis-(2-hydroxyethyl)-p-phenylenediamine, 4-amino-3-methylphenol, 4-amino-2-((diethylamino)-methyl)-phenol, 2-aminomethyl-4-aminophenol, 2,4,5,6-tetraminopyrimidine, 2-hydroxy-4,5,6-triaminopyrimidine, 4-hydroxy-2,5,6-triaminopyrimidine or 4,5-diamino-1-(2'-hydroxyethyl)-pyrazole, or combinations thereof.

15. The composition of claim 14 further comprising at least one secondary intermediate, wherein the secondary intermediate comprises 1-naphthol, 1,5-dihydroxynaphthalene, 2,7-dihydroxynaphthalene, 1,7-dihydroxynaphthalene, 3-aminophenol, 5-amino-2-methylphenol, resorcinol, 4-chlororesorcinol, 2-chloro-6-methyl-3-aminophenol, 2-methyl resorcinol, 5-methyl resorcinol, 2,5-dimethyl resorcinol or 2,6-dihydroxy-3,4-diaminopyridine, or combinations thereof.

16. The composition of claim 13 further comprising at least one secondary intermediate, wherein the secondary intermediate comprises 1-naphthol, 1,5-dihydroxynaphthalene, 2,7-dihydroxynaphthalene, 1,7-dihydroxynaphthalene, 3-aminophenol, 5-amino-2-methylphenol, resorcinol, 4-chlororesorcinol, 2-chloro-6-methyl-3-aminophenol, 2-methyl resorcinol, 5-methyl resorcinol, 2,5-dimethyl resorcinol or 2,6-dihydroxy-3,4-diaminopyridine, or combinations thereof.

17. The composition of claim 13 wherein the compound corresponding to formula (I) comprises 1-(N-cycloheptylamino)-2-nitro-4-aminobenzene or 1-(N-cyclooctylamino)-2-nitro-4-aminobenzene, or combinations thereof.

18. The composition of claim 1 further comprising at least one anionic polymer, nonionic polymer or cationic polymer, or combinations thereof.

19. A method for coloring or tinting keratin fibers comprising applying to keratin fibers the coloring or tinting composition of claim 1.

20. A compound corresponding to formula I:

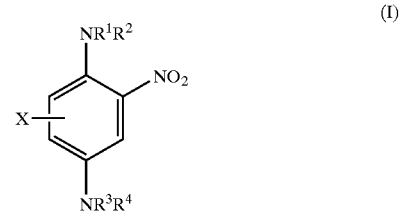

wherein R¹ is a cycloheptyl group, R² to R⁴ are hydrogen, and X is hydrogen.

21. A compound corresponding to formula I:

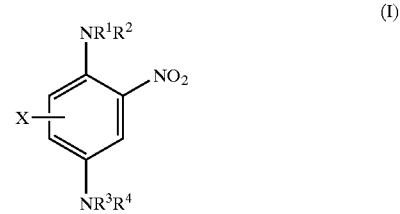

wherein R¹ is a cyclooctyl group, R² to R⁴ are hydrogen, and X is hydrogen.

* * * * *